US012624001B2

(12) United States Patent
Hashimoto

(10) Patent No.: US 12,624,001 B2
(45) Date of Patent: May 12, 2026

(54) METHOD FOR PRODUCING THIOL COMPOUND

(71) Applicant: SHOWA DENKO K.K., Tokyo (JP)

(72) Inventor: Yuji Hashimoto, Yokohama (JP)

(73) Assignee: Resonac Corporation, Tokyo (JP)

( * ) Notice: Subject to any disclaimer, the term of this patent is extended or adjusted under 35 U.S.C. 154(b) by 622 days.

(21) Appl. No.: 17/928,486

(22) PCT Filed: May 31, 2021

(86) PCT No.: PCT/JP2021/020600

§ 371 (c)(1),
(2) Date: Nov. 29, 2022

(87) PCT Pub. No.: WO2021/246349

PCT Pub. Date: Dec. 9, 2021

(65) Prior Publication Data

US 2023/0202976 A1 Jun. 29, 2023

(30) Foreign Application Priority Data

Jun. 1, 2020 (JP) ................................ 2020-095577

(51) Int. Cl.
*C07C 319/28* (2006.01)
*C07D 251/34* (2006.01)

(52) U.S. Cl.
CPC .......... *C07C 319/28* (2013.01); *C07D 251/34* (2013.01)

(58) Field of Classification Search
CPC .................................................. C07C 319/28
See application file for complete search history.

(56) References Cited

FOREIGN PATENT DOCUMENTS

| | | | | |
|---|---|---|---|---|
| JP | 1-172369 | * | 7/1989 | ........... C07C 319/12 |
| JP | 01-172369 A | | 7/1989 | |
| JP | 1-231040 | * | 9/1989 | ........... C07C 319/12 |
| JP | 01-231040 A | | 9/1989 | |
| JP | 2011-084479 | * | 4/2011 | ........... C07C 319/12 |
| JP | 2011-084479 A | | 4/2011 | |
| JP | 2015-093887 A | | 5/2015 | |
| JP | 5713886 B2 | | 5/2015 | |
| JP | 5801556 B2 | | 10/2015 | |
| JP | 2016-012131 A | | 1/2016 | |
| JP | 2016-104875 A | | 6/2016 | |
| JP | 2017-043721 A | | 3/2017 | |
| JP | 6184003 B2 | | 8/2017 | |
| JP | 6468315 B2 | | 2/2019 | |

OTHER PUBLICATIONS

"1,6-Hexanedithiol(1191-43-1)", Chemical Book, 2017, online, Retrieved on Jun. 18, 2021, Retrieved from the Internet: URL: https://www.chemicalbook.com/ProductMSDSDetailCB1219809_EN.htm, pp. 1-4.
International Search Report for PCT/JP2021/020600 dated Jul. 6, 2021.
International Preliminary Report on Patentability for PCT/JP2021/020600 issued Dec. 6, 2022 with English Translation of Written Opinion of the International Searching Authority.

* cited by examiner

*Primary Examiner* — Paul V Ward
(74) *Attorney, Agent, or Firm* — Sughrue Mion, PLLC

(57) ABSTRACT

A method for producing a thiol compound including a light emission process in which light is emitted to a colored thiol compound or a composition containing the thiol compound. In the light emission process, it is preferable to emit light including light with a wavelength of 250 nm to 600 nm to the composition.

16 Claims, No Drawings

METHOD FOR PRODUCING THIOL COMPOUND

CROSS REFERENCE TO RELATED APPLICATIONS

This application is a National Stage of International Application No. PCT/JP2021/020600 filed May 31, 2021, claiming priority based on Japanese Patent Application No. 2020-095577 filed Jun. 1, 2020, the content of which is incorporated herein by reference.

TECHNICAL FIELD

The present invention relates to a method for producing a thiol compound.

BACKGROUND ART

In recent years, in order to save energy and improve productivity, there has been a demand for a curable resin with favorable curability that cures quickly with little energy. As such a curable resin, a curable resin containing thiols is being focused on. For example, Patent Document 1 and Patent Document 2 describe photocurable resin compositions containing a thiol compound. Patent Document 3 describes that a resin composition containing a thiol compound is photocured and then thermally cured. Patent Document 4 to Patent Document 7 describe resin compositions containing a thiol compound and having excellent low-temperature curability.

In addition, Patent Document 8 describes a production method for producing a mercaptocarboxylic acid polyhydric alcohol ester according to an esterification reaction of mercaptocarboxylic acid or mercaptocarboxylic acid ester and a polyhydric alcohol. Patent Document 8 describes that the produced tetrakis(3-mercaptobutanoic acid) pentaerythritol ester is a light yellow liquid.

CITATION LIST

Patent Document

[Patent Document 1]
Japanese Patent No. 5801556

[Patent Document 2]
Japanese Patent No. 6468315

[Patent Document 3]
Japanese Patent No. 6184003

[Patent Document 4]
Japanese Unexamined Patent Application, First Publication No. 2015-93887

[Patent Document 5]
Japanese Unexamined Patent Application, First Publication No. 2017-43721

[Patent Document 6]
Japanese Unexamined Patent Application, First Publication No. 2016-12131

[Patent Document 7]
Japanese Unexamined Patent Application, First Publication No. 2016-104875

[Patent Document 8]
Japanese Unexamined Patent Application, First Publication No. 2011-084479

[Patent Document 9]
Japanese Patent No. 5713886

SUMMARY OF INVENTION

Technical Problem

In the related art, curable resins used for specific applications have been required to have little coloring and excellent transparency. Specific applications are, for example, optical materials, and the outer surfaces of final products.

In recent years, it has been required to improve curability of curable resins used for such specific applications. However, thiol compounds are typically colored yellow, orange, brown, red or the like in some cases. It is difficult for a curable resin that requires transparency to contain a colored thiol compound in order to improve curability. Therefore, there is a need for a technique for reducing coloring of thiol compounds.

The present invention has been made in view of the above circumstances, and an object of the present invention is to provide a method for producing a thiol compound by which it is possible to reduce coloring of the thiol compound.

Solution to Problem

[1] A method for producing a thiol compound, including a light emission process in which light is emitted to a colored thiol compound or a composition containing the thiol compound.

[2] The method for producing a thiol compound according to [1], wherein the light includes light with a wavelength of 250 nm to 600 nm.

[3] The method for producing a thiol compound according to [1] or [2],
wherein the Hazen color number of the thiol compound or the composition is 100 or more, and
wherein the light emission process is performed until the Hazen color number of the thiol compound or the composition is less than 100.

[4] The method for producing a thiol compound according to any one of [1] to [3],
wherein the thiol compound includes a thiol having at least one secondary mercapto group.

[5] The method for producing a thiol compound according to any one of [1] to [3],
wherein the thiol compound includes one or both of 3-mercaptocarboxylic acid and 3-mercaptocarboxylic acid ester.

[6] The method for producing a thiol compound according to [5],
wherein the thiol compound includes one or both of 3-mercaptobutanoic acid and 3-mercaptobutanoic acid ester.

[7] The method for producing a thiol compound according to [6],
wherein the 3-mercaptobutanoic acid ester is any one of compounds represented by the following Formulae (1) to (4):

[Chem. 1]

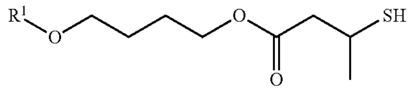

(1)

-continued (2)

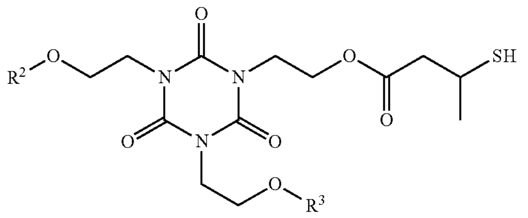

(3)

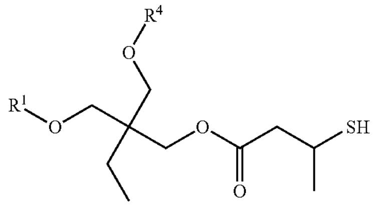

(4)

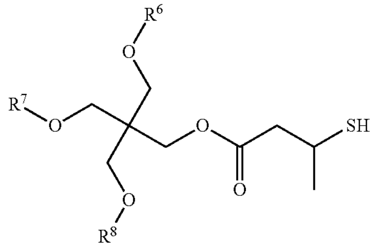

(5)

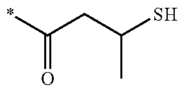

(in Formula (1), $R^1$ represents a hydrogen atom or a group represented by Formula (5)) (in Formula (2), $R^2$ and $R^3$ each independently represent a hydrogen atom or a group represented by Formula (5))

(in Formula (3), $R^4$ and $R^5$ each independently represent a hydrogen atom or a group represented by Formula (5))

(in Formula (4), $R^6$, $R^7$, and $R^8$ each independently represent a hydrogen atom or a group represented by Formula (5))

(in Formula (5), * indicates bonding positions for compounds represented by Formulae (1) to (4)).

[8] The method for producing a thiol compound according to [6], wherein the 3-mercaptobutanoic acid ester is any one of compounds represented by the following Formulae (6) to (9):

[Chem. 2]

(6)

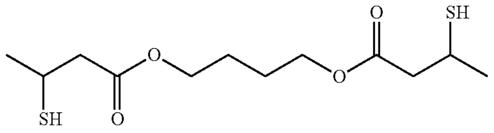

-continued (7)

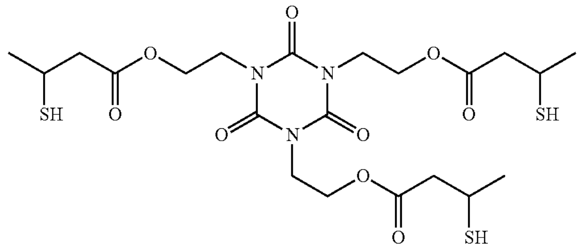

(8)

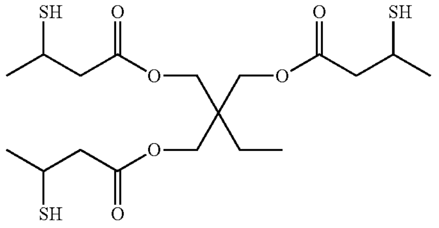

(9)

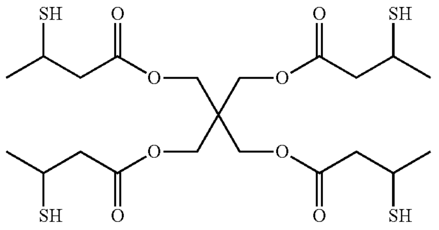

[9] The method for producing a thiol compound according to any one of [1] to [8], wherein the composition contains the thiol compound and at least one solvent selected from the group consisting of toluene, xylene, cyclohexane, methylcyclohexane, acetonitrile, methanol, ethanol, n-propanol, isopropanol, n-butanol, isobutanol, methyl acetate, ethyl acetate, butyl acetate, acetone, methyl ethyl ketone, methyl isobutyl ketone, cyclohexanone, ethylene glycol dimethyl ether, ethylene glycol monoethyl ether, ethylene glycol monobutyl ether, ethylene glycol monobutyl ether acetate, propylene glycol monomethyl ether, propylene glycol monomethyl ether acetate, and water.

Advantageous Effects of Invention

The method for producing a thiol compound of the present invention includes a light emission process in which light is emitted to a colored thiol compound or a composition containing the colored thiol compound. Therefore, according to the method for producing a thiol compound of the present invention, it is possible to reduce coloring of the thiol compound.

DESCRIPTION OF EMBODIMENTS

In order to address the above problems, the inventors conducted extensive studies as described below.

Generally, compounds are stored in a light shielding environment. This is to prevent the compounds from deteriorating due to light energy. Since it is thought that thiol compounds deteriorate when exposed to light, they are stored in a light shielding environment like general compounds.

However, the inventors conducted extensive studies and as a result, found that, when colored thiol compounds are exposed to light, the thiol compounds are decolorized.

It is presumed that a change occurs in colored thiol compounds because unspecified impurities are decomposed with light energy and become colorless substances. Generally, the thiol compound contains impurities such as by-products produced during synthesis and excess raw materials. As necessary, the thiol compound is purified during and/or after production. Therefore, the amount of impurities contained in the thiol compound used for the material of the curable resin is very small. However, details of impurities that color the thiol compound which is inherently colorless and transparent have not been clarified. Therefore, the removal method is also unknown, and it is presumed that there are cases in which removal is not sufficient.

Therefore, the inventors conducted further studies and confirmed that, when light is emitted to a colored thiol compound or a composition containing the same, regardless of the type of the thiol compound, it is possible to reduce coloring of the thiol compound and completed the present invention.

Hereinafter, a method for producing a thiol compound of the present invention will be described in detail. Here, the present invention is not limited to only the following embodiments.

The method for producing a thiol compound of the present embodiment includes a light emission process in which light is emitted to a colored thiol compound or a composition containing the same.

"Colored Thiol Compound"

The colored thiol compound contains unspecified impurities. The colored thiol compound is not particularly limited as long as it is a thiol compound having a higher Hazen color number than a pure substance. For example, the colored thiol compound has a Hazen color number of 100 or more, and the Hazen color number may be 80 or more, 40 or more, or 20 or more. Generally, if the Hazen color number is 10 or more, coloring can be visually confirmed.

The colored thiol compound has at least one mercapto group. The mercapto group may be any of a primary mercapto group, a secondary mercapto group, and a tertiary mercapto group. The colored thiol compound may have two or more mercapto groups selected from among a primary mercapto group, a secondary mercapto group, and a tertiary mercapto group. Only one colored thiol compound, or two or more thereof may be used.

Examples of thiol compounds having a primary mercapto group include 3-mercaptopropionic acid, 3-mercaptopropionic acid ester, bisphenol A type thiol, and polyether polymer type thiol.

Examples of 3-mercaptopropionic acid ester include esters of an alcohol selected from the group consisting of 1,4-butanediol, 1,3,5-tris(2-hydroxyethyl)-1,3,5-triazine-2,4,6 (1H,3H,5H)-trione, trimethylolpropane and pentaerythritol, and 3-mercaptopropionic acid. Specifically, pentaerythritol tetrakis(3-mercaptopropionate), trimethylolpropane tris(3-mercaptopropionate) or the like can be used.

As the bisphenol A type thiol, for example, bisphenol A type thiol QX11 (commercially available from Mitsubishi Chemical Corporation) can be used.

As the polyether polymer type thiol, for example, a polyether polymer type thiol CAPCURE 3-800 (commercially available from Cognis) can be used.

Examples of thiol compounds having a secondary mercapto group include 3-mercaptobutanoic acid and 3-mercaptobutanoic acid ester. Examples of 3-mercaptobutanoic acid ester include esters of an alcohol selected from the group consisting of 1,4-butanediol, 1,3,5-tris(2-hydroxyethyl)-1,3,5-triazine-2,4,6 (1H,3H,5H)-trione, trimethylolpropane and pentaerythritol, and 3-mercaptobutanoic acid.

Preferably, the colored thiol compound contains a thiol having at least one secondary mercapto group.

The colored thiol compound preferably contains one or both of 3-mercaptocarboxylic acid and 3-mercaptocarboxylic acid ester, and more preferably contains one or both of 3-mercaptobutanoic acid and 3-mercaptobutanoic acid ester.

Specifically, 3-mercaptobutanoic acid ester is preferably any one of compounds represented by the following Formulae (1) to (4). When the colored thiol compound contains any compounds represented by the following (1) to (4), an effect of reducing coloring of the thiol compound due to light emission is significant.

[Chem. 1]

(1)

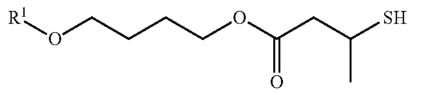

(2)

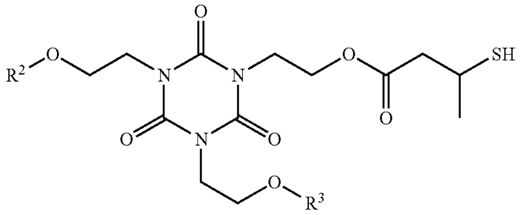

(3)

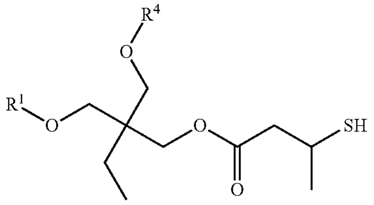

(4)

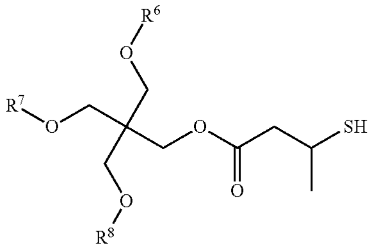

(5)

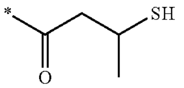

(in Formula (1), $R^1$ represents a hydrogen atom or a group represented by Formula (5)) (in Formula (2), $R^2$ and $R^3$ each independently represent a hydrogen atom or a group represented by Formula (5))

(in Formula (3), $R^4$ and $R^5$ each independently represent a hydrogen atom or a group represented by Formula (5))

(in Formula (4), $R^6$, $R^7$, and $R^8$ each independently represent a hydrogen atom or a group represented by Formula (5))

(in Formula (5), * indicates bonding positions for compounds represented by Formulae (1) to (4)).

More preferably, the 3-mercaptobutanoic acid ester is any one of 1,4-bis(3-mercaptobutyryloxy) butane represented by the following Formula (6), 1,3,5-tris(2-(3-sulfanylbutanoyloxy)ethyl)-1,3,5-triazine-2,4,6-trione represented by the following Formula (7), trimethylolpropane tris(3-mercaptobutyrate) represented by the following Formula (8), and pentaerythritol tetrakis(3-mercaptobutyrate) represented by the following Formula (9).

[Chem. 2]

(6)

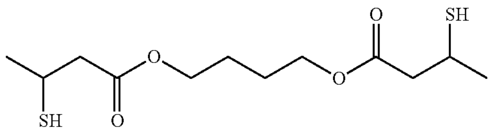

(7)

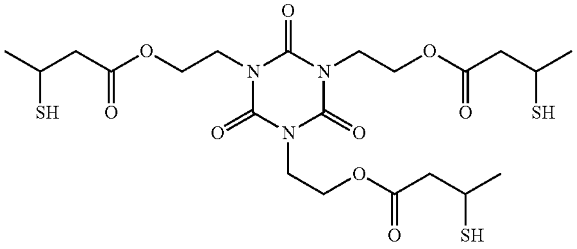

(8)

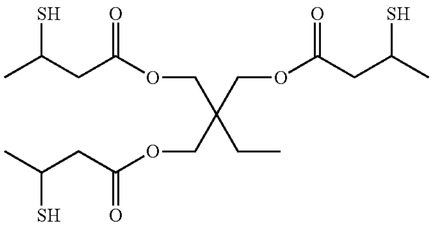

(9)

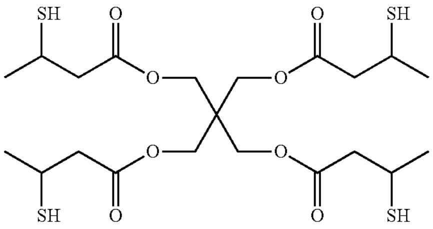

The thiol compound can be produced by a conventionally known method.

For example, as described in Patent Document 9,3-mercaptocarboxylic acid such as 3-mercaptobutanoic acid can be synthesized by a method of reacting an α,β-unsaturated carboxylic acid and hydrogen sulfide in an aqueous solution in the presence of a basic compound.

For example, a 3-mercaptobutanoic acid ester such as compounds represented by Formulae (6) to (9) can be synthesized by a method of synthesizing 3-mercaptobutanoic acid and then performing an esterification reaction of 3-mercaptobutanoic acid and a polyhydric alcohol as described in Patent Document 8.

(Composition)

The composition in the present embodiment contains a colored thiol compound, and as necessary, contains a solvent and/or a compound other than the thiol compound. The Hazen color number of the composition containing a colored thiol compound is, for example, 100 or more. The Hazen color number of the composition containing a colored thiol compound may be 80 or more, 40 or more or 20 or more. Generally, if the Hazen color number is 10 or more, coloring can be visually confirmed.

[Solvent]

The composition in the present embodiment may contain, as necessary, a solvent. The solvent can be appropriately selected according to the type of the thiol compound and the wavelength of light emitted in the light emission process.

As the solvent, for example, organic solvents such as hydrocarbon, alcohol, ester, ketone, and ether and/or water can be used. Specifically, it is preferable to use at least one selected from the group consisting of toluene, xylene, cyclohexane, methylcyclohexane, acetonitrile, methanol, ethanol, n-propanol, isopropanol, n-butanol, isobutanol, methyl acetate, ethyl acetate, butyl acetate, acetone, methyl ethyl ketone, methyl isobutyl ketone, cyclohexanone, ethylene glycol dimethyl ether, ethylene glycol monoethyl ether, ethylene glycol monobutyl ether, ethylene glycol monobutyl ether acetate, propylene glycol monomethyl ether, propylene glycol monomethyl ether acetate, and water. Among these solvents, acetonitrile and water do not exhibit strong absorption of light in a wavelength range of 200 nm or more and allow light emitted in the light emission process to be easily transmitted. Therefore, when the solvent is acetonitrile and/or water, this is preferable because light is easily and efficiently emitted to the thiol compound in the light emission process.

When the thiol compound is a solid at room temperature (25° C.), it is preferable to emit light to a composition in which the thiol compound is dissolved or dispersed in a solvent. When the composition contains a thiol compound that is a solid at room temperature and a solvent for dissolving or dispersing it, light is more uniformly emitted to the thiol compound without unevenness in the light emission process than when no solvent is contained. As a result, it is possible to reduce coloring of the thiol compound with less light energy.

Even if the thiol compound is a highly viscous liquid at room temperature (25° C.), it is preferable to emit light to a composition in which the thiol compound is dissolved or dispersed in a solvent. When the composition contains a thiol compound that is a highly viscous liquid at room temperature and a solvent for dissolving or dispersing it, light is more uniformly emitted to the thiol compound without unevenness in the light emission process than when no solvent is contained. As a result, it is possible to reduce coloring of the thiol compound with less light energy.

In addition, even if coloring of the thiol compound is significant (for example, the Hazen color number is 150 or more), the thiol compound may be diluted with a solvent to prepare a composition before the light emission process is performed. Thereby, compared to when the light emission process is performed only on the thiol compound, the concentration of the thiol compound in the liquid becomes low, and light is emitted with efficiently and uniformly. As a result, it is possible to shorten the light emission time for light emitted and/or weaken the light emission intensity in the light emission process.

When the composition contains a solvent, the content of the solvent in the composition is not particularly limited, and may be, for example, 10 to 90 mass %, and is preferably 30 to 70 mass % and more preferably 40 to 60 mass %, and can be appropriately determined according to the type of the thiol compound. When the content of the solvent in the composition is 30 mass % or more, the effect of light reaching the inside according to dilution becomes significant, and light can be uniformly and efficiently emitted to the thiol compound in the light emission process. In addition, when the content of the solvent in the composition is 70 mass % or less, it is possible to reduce the amount of the solvent consumed, and the light emission process can be performed more efficiently in a smaller facility. In addition, if the content of the solvent in the composition is 70 mass % or less, when the solvent is removed after the light emission process, the solvent can be easily removed, and processing can become efficient when the solvent is collected and reused.

[Compound Other than Thiol Compound]

The composition containing a thiol compound in the present embodiment may contain, as necessary, other compounds that are neither a thiol compound nor a solvent. Other compounds include, for example, by-products produced during synthesis of thiol compounds, excess raw materials, stabilizers, and pH adjusting agents, and can be determined according to applications of thiol compounds after the light emission process and the like and are not particularly limited.

When the composition contains compounds other than the thiol compound, the content of other compounds in the composition is not particularly limited, and may be, for example, 0.1 to 10 mass %, and can be appropriately determined according to the type of the thiol compound.

Preferably, the composition contains no polymer. Here, the polymer is a component in which 5 or more monomers, typically 10 or more monomers, are bonded. When the composition contains a polymer, it becomes difficult to obtain a decolorization effect according to light emission. More specifically, the polymerized substance has restricted molecule movement and generally poor or no fluidity. Therefore, it is known that a chemical reaction is less likely to occur in a composition containing this. Accordingly, even when light is emitted to the composition containing a polymer, it is presumed that unspecified impurities contained in the composition are difficult to decompose. The content of the polymer in the composition is preferably 10 mass % or less and more preferably 5 mass % or less.

In addition, preferably, the composition contains no photopolymer. This is because, in addition to the fact that movement of molecules of the photopolymer is restricted, it is difficult to obtain a decolorization effect according to light emission for the following reason. The photopolymer generally contains compounds such as a photopolymerization initiator and its decomposition product. These compounds are colored when excess light is emitted in many cases. Therefore, when light is emitted to a composition containing a photopolymer, not only unspecified impurities contained in the composition are decomposed, but also these compounds are colored conversely, and it is presumed that it is difficult to obtain a decolorization effect. The content of the photopolymer in the composition is preferably 10 mass % or less and more preferably 5 mass % or less.

[Light Emission Process]

In the light emission process of the present embodiment, light is emitted to a colored thiol compound or a composition containing the colored thiol compound. In the process of producing a thiol compound of the present embodiment, the light emission process can be performed once or a plurality of times.

In the light emission process, the wavelength of light emitted can be appropriately determined according to the type of the thiol compound and the formulation of the composition. In the present embodiment, the light emitted preferably includes light with a wavelength of 250 nm to 600 nm. Light with a wavelength of 250 nm or more is preferable because it is less likely to be blocked by absorption of the thiol compound and the organic solvent. In addition, light with a wavelength of 600 nm or less is preferable because it has sufficient energy at which coloring of the thiol compound can be reduced. Since light emitted can effectively reduce coloring of the colored thiol compound, it is more preferable to contain light in a wavelength range of 300 nm to 550 nm, and still more preferable to contain light in a range of 350 to 500 nm.

The type of the light source used in the light emission process is not particularly limited. Specifically, as the light source, sunlight, an incandescent lamp, a fluorescent lamp, a light-emitting diode (LED) lamp or the like can be used. Among these light sources, sunlight can be particularly preferably used because it has a high light emission intensity, includes light in a wide wavelength range, and does not require energy supply from a power source or the like.

The method of evaluating coloring is not particularly limited, but the Hazen color number (APHA) can be preferably used because the color of the colored thiol compound is typically yellow. As a method of determining the Hazen color number, for example, a measurement method using a spectrometer may be used, or a method using a colorimetric tube may be used.

The amount of change in the Hazen color number (APHA) of a measurement target (a colored thiol compound or a composition containing a colored thiol compound) when the light emission process is performed can be adjusted according to the wavelength of light to be emitted, a light emission intensity, and an emission amount (light emission time) with respect to the formulation and amount of the colored thiol compound or the composition containing the same. As the energy of light emitted in the light emission process is stronger and the amount thereof is larger, an effect of reducing coloring of the colored thiol compound is stronger.

For example, when the Hazen color number (APHA) of the thiol compound or the composition containing the same is 100 or more, the light emission process is preferably performed until the Hazen color number becomes less than 100. In this case, the thiol compound after the light emission process can be preferably used for applications as resin raw materials such as optical materials, exterior materials, and paints. Since a thiol compound more suitable for these applications is obtained, the light emission process is more preferably performed until the Hazen color number becomes 80 or less, and still more preferably performed until the Hazen color number becomes 60 or less.

Even if the Hazen color number (APHA) of the thiol compound or the composition containing the same is less than 100, the light emission process may be performed in order to further reduce coloring. For example, when the Hazen color number is 80 or more, the light emission process may be performed until the Hazen color number becomes less than 80, more preferably until the Hazen color number becomes 70 or less, and still more preferably until the Hazen color number becomes 60 or less. When the Hazen color number is 60 or more, the light emission process may be performed until the Hazen color number becomes less than 60, more preferably until the Hazen color number becomes 50 or less, and still more preferably until the Hazen color number becomes 40 or less.

As the container for accommodating the thiol compound or the composition containing the same when the light emission process is performed, for example, a resin container made of polypropylene or the like, a glass container or the like can be used, and the material and the shape are not particularly limited. As the container, when light is emitted from the outside of the container to the thiol compound or the composition containing the same in the container in the light emission process, it is preferable to use a container having favorable permeability of light with a wavelength to be emitted.

The light emission process is preferably performed while stirring the thiol compound or the composition containing the same accommodated in the container. Thereby, it is possible to efficiently reduce coloring of the colored thiol compound without unevenness, and it is possible to efficiently dissipate heat applied from the light source to the thiol compound or the composition containing the same.

The temperature, the pressure, and other conditions when the light emission process is performed are not particularly limited.

The thiol compound or the composition containing the same after the light emission process can be directly used as the resin raw material such as optical materials, exterior materials, and paints. When the composition after the light emission process contains a solvent, as necessary, the solvent may be removed using a known method. In addition, when the composition after the light emission process contains compounds other than the thiol compound, as necessary, the other compounds may be removed using a known method.

The thiol compound after the light emission process may be used as an intermediate product.

For example, the thiol compound after the light emission process may be 3-mercaptocarboxylic acid synthesized as an intermediate product in the process of synthesizing 3-mercaptocarboxylic acid ester such as 3-mercaptobutanoic acid ester. When 3-mercaptocarboxylic acid ester is produced by a method of esterifying 3-mercaptocarboxylic acid after the light emission process, a less colored product is obtained.

The method for producing a thiol compound of the present embodiment includes a light emission process in which light is emitted to the colored thiol compound or the composition containing the same. Therefore, according to the method for producing a thiol compound of the present embodiment, it is possible to reduce coloring of the thiol compound.

The method for producing a thiol compound of the present embodiment can be easily performed by adding the light emission process to the conventional method for producing a thiol compound without changing the conventional method for producing a thiol compound.

In addition, the light emission process in the method for producing a thiol compound of the present embodiment can be easily performed without requiring a special facility and using sunlight as a light source.

In addition, the method for producing a thiol compound of the present embodiment can be performed without using compounds such as a decoloring agent and an adsorbing agent. Therefore, for example, this is preferable because there are no contamination of impurities and foreign substances caused by newly added compounds compared to when compounds such as a decoloring agent and/or an adsorbing agent are added to the colored thiol compound or the composition containing the same.

EXAMPLES

Hereinafter, the present invention will be described in more detail with reference to examples and comparative examples. Here, the following examples are intended to facilitate understanding of the content of the present invention, and the present invention is not limited only to these examples.

The following examples and comparative examples were performed at room temperature (25° C.) unless otherwise specified.

In the following examples and comparative examples, the Hazen color number (APHA) was determined using a spectrophotometer SD6000 (commercially available from Nippon Denshoku Industries Co., Ltd.). The Hazen color number was corrected using solutions obtained by diluting a chromatility standard solution (1,000 degrees) (for chromaticity test, commercially available from Kanto Chemical Co., Inc.) with pure water and having an APHA of 500, 200, 100, 50, 20, 10, and 5 and pure water (with an APHA of 0).

Example 1

A compound represented by Formula (9) was synthesized according to the method described in Patent Document 8. The Hazen color number (APHA) of the synthesized compound represented by Formula (9) was obtained. As a result, the APHA was 160.

A light emission process of emitting light was performed on the compound having an APHA of 160 and represented by Formula (9) by the following method.

That is, 50 mL (60 g) of the compound having an APHA of 160 and represented by Formula (9) was put into a semitransparent polypropylene container (Iboy (registered trademark), 50 mL wide-mouth bottle, commercially available from As One Corporation) and sealed. Then, the container was placed under a light source (white LED; LED base light TENQOO (product name); commercially available from Toshiba Lighting & Technology Corporation), and light was emitted to the compound represented by Formula (9) through the container.

As shown in Table 1, the Hazen color number (APHA) of the compound represented by Formula (9) decreased over time after light emission started and the APHA became 72 after 30 days. Then, the container was left in a dark place for 12 days, but the Hazen color number of the compound represented by Formula (9) did not change. Accordingly, it was confirmed that the compound represented by Formula (9) was less colored when light was emitted using a white LED and was not colored even after being stored in a dark place.

TABLE 1

| | Time [days] | 0 | 2 | 7 | 12 | 16 | 22 | 30 |
|---|---|---|---|---|---|---|---|---|
| Example 1 | APHA | 160 | 114 | 94 | 85 | 80 | 75 | 72 |
| Example 2 | | 160 | 76 | 54 | 41 | 33 | 26 | 23 |
| Comparative Example 1 | | 160 | 160 | 160 | 161 | 160 | 159 | 158 |

Example 2

50 mL (60 g) of the same compound having an APHA of 160 and represented by Formula (9) as in Example 1 was put into the same container as in Example 1 and sealed. Then, the container was left on a south-facing window exposed to sunlight, and light was emitted to the compound represented by Formula (9) through the container.

As shown in Table 1, the Hazen color number (APHA) of the compound represented by Formula (9) decreased over time after light emission started, and the APHA became 23 after 30 days. Then, the container was left in a dark place for 12 days. As a result, the APHA of the compound represented by Formula (9) became 22 and hardly changed. Accordingly, it was confirmed that the compound represented by Formula (9) was less colored when sunlight was emitted and was not colored even after being stored in a dark place.

Comparative Example 1

50 mL (60 g) of the same compound having an APHA of 160 and represented by Formula (9) as in Example 1 was put into the same container as in Example 1 and sealed. Then, the container was wrapped with an aluminum foil and light-shielded, and left under a light source (white LED) as in Example 1, and light was emitted to the container wrapped with an aluminum foil.

As shown in Table 1, the Hazen color number (APHA) of the compound represented by Formula (9) hardly changed even when light was emitted, and the APHA was 158 after 30 days. Then, the container was left in a dark place for 12 days. As a result, the APHA of the compound represented by Formula (9) was 160.

Example 3

A liquid was prepared by mixing the same compound having an APHA of 160 and represented by Formula (9) as in Example 1 and toluene (commercially available from Junsei Chemical Co., Ltd., special grade) at a volume ratio of 1:1. The Hazen color number (APHA) of the obtained mixed solution was obtained, and the result was an APHA of 67. 50 mL of the mixed solution was measured and put into the same container as in Example 1 and sealed. Then, the container was left under the same light source (white LED) as in Example 1, and light was emitted to the mixed solution through the container.

As shown in Table 2, the Hazen color number (APHA) of the mixed solution decreased over time after light emission started, and the APHA became 37 after 12 days.

TABLE 2

| | Time [days] | 0 | 4 | 7 | 12 |
|---|---|---|---|---|---|
| Example 3 | APHA | 67 | 43 | 41 | 37 |
| Example 4 | | 100 | 46 | 44 | 37 |

Example 4

A mixed solution was prepared in the same manner as in Example 3 except that acetonitrile (special grade reagent, commercially available from FUJIFILM Wako Pure Chemical Corporation) was used in place of toluene. The Hazen color number (APHA) of the obtained mixed solution was obtained, and the result was an APHA of 100. 50 mL of the mixed solution was measured and put into the same container as in Example 1 and sealed. Then, the container was left under the same light source (white LED) as in Example 1, and light was emitted to the mixed solution through the container.

As shown in Table 2, the Hazen color number (APHA) of the mixed solution decreased over time after light emission started, and the APHA became 37 after 12 days.

Example 5

The Hazen color number (APHA) of the compound represented by Formula (6) (Karenz M T (registered trademark) BD1 (commercially available from Showa Denko K. K.)) was obtained. As a result, the APHA was 57. 30 mL (33 g) of the compound having an APHA of 57 and represented by Formula (6) was put into the same container as in Example 1 and sealed. Then, the container was left under the same light source (white LED) as in Example 1, and light was emitted to the compound represented by Formula (6) through the container.

As shown in Table 3, the Hazen color number (APHA) of the compound represented by Formula (6) decreased over time after light emission started and the APHA became 38 after 8 days.

TABLE 3

| | Time [days] | 0 | 1 | 3 | 8 |
|---|---|---|---|---|---|
| Example 5 | APHA | 57 | 48 | 43 | 38 |
| Example 6 | | 45 | 39 | 40 | 36 |
| Example 7 | | 42 | 38 | 34 | 31 |
| Example 8 | | 57 | 44 | 36 | 32 |
| Example 9 | | 25 | 23 | 16 | 14 |
| Comparative Example 2 | | 57 | 56 | 56 | 58 |
| Comparative Example 3 | | 45 | 46 | 46 | 46 |
| Comparative Example 4 | | 42 | 42 | 42 | 42 |
| Comparative Example 5 | | 57 | 57 | 58 | 56 |
| Comparative Example 6 | | 25 | 25 | 24 | 25 |

Comparative Example 2

30 mL (33 g) of the same compound having an APHA of 57 and represented by Formula (6) as in Example 5 was put into the same container as in Example 1 and sealed. Then, the container was wrapped with an aluminum foil and light-shielded and left under a light source (white LED) as in Example 1, and light was emitted to the container wrapped with an aluminum foil.

As shown in Table 3, the Hazen color number (APHA) of the compound represented by Formula (6) hardly changed even when light was emitted and the APHA was 58 after 8 days.

Example 6

The Hazen color number (APHA) of the compound represented by Formula (7) (Karenz M T (registered trademark) NR1 (commercially available from Showa Denko K. K.)) was obtained. As a result, the APHA was 45. 30 mL (38 g) of the compound having an APHA of 45 and represented by Formula (7) was put into the same container as in Example 1 and sealed. Then, the container was left under the same light source (white LED) as in Example 1, and light was emitted to the compound represented by Formula (7) through the container.

As shown in Table 3, the Hazen color number (APHA) of the compound represented by Formula (7) decreased over time after light emission started, and the APHA became 36 after 8 days.

Comparative Example 3

30 mL (38 g) of the compound having an APHA of 45 and represented by Formula (7) as in Example 6 was put into the same container as in Example 1 and sealed. Then, the container was wrapped with an aluminum foil and light-shielded and left under a light source (white LED) as in Example 1, and light was emitted to the container wrapped with an aluminum foil.

As shown in Table 3, the Hazen color number (APHA) of the compound represented by Formula (7) hardly changed even when light was emitted, and the APHA was 46 after 8 days.

Example 7

The Hazen color number (APHA) of the compound represented by Formula (8) (Karenz M T (registered trademark) TPMB (commercially available from Showa Denko K. K.)) was obtained. As a result, the APHA was 42. 30 mL (34 g) of the compound having an APHA of 42 and represented by Formula (8) was put into the same container as in Example 1 and sealed. Then, the container was left under the same light source (white LED) as in Example 1, and light was emitted to the compound represented by Formula (8) through the container.

As shown in Table 3, the Hazen color number (APHA) of the compound represented by Formula (8) decreased over time after light emission started, and the APHA became 31 after 8 days.

Comparative Example 4

30 mL (34 g) of the same compound having an APHA of 42 and represented by Formula (8) as in Example 7 was put into the same container as in Example 1 and sealed. Then, the container was wrapped with an aluminum foil and light-shielded and left under a light source (white LED) as in Example 1, and light was emitted to the container wrapped with an aluminum foil.

As shown in Table 3, the Hazen color number (APHA) of the compound represented by Formula (8) did not change even when light was emitted, and the APHA was 42 after 8 days.

Example 8

The Hazen color number (APHA) of the compound represented by Formula (9) (Karenz M T (registered trademark) PE1 (commercially available from Showa Denko K. K.)) was obtained. As a result, the APHA was 57. 30 mL (36 g) of the compound having an APHA of 57 and represented by Formula (9) was put into the same container as in Example 1 and sealed. Then, the container was left under the same light source (white LED) as in Example 1, and light was emitted to the compound represented by Formula (9) through the container.

As shown in Table 3, the Hazen color number (APHA) of the compound represented by Formula (9) decreased over time after light emission started, and the APHA become 32 after 8 days.

Comparative Example 5

30 mL (36 g) of the same compound having an APHA of 57 and represented by Formula (9) as in Example 8 was put into the same container as in Example 1 and sealed. Then, the container was wrapped with an aluminum foil and light-shielded and left under a light source (white LED) as in Example 1, and light was emitted to the container wrapped with an aluminum foil.

As shown in Table 3, the Hazen color number (APHA) of the compound represented by Formula (9) hardly changed even when light was emitted, and the APHA was 56 after 8 days.

Example 9

3-mercaptobutanoic acid was synthesized by the method described in Patent Document 9. The Hazen color number (APHA) of the synthesized 3-mercaptobutanoic acid was obtained. As a result, the APHA was 25. 30 mL (34 g) of 3-mercaptobutanoic acid having an APHA of 25 was put into the same container as in Example 1 and sealed. Then, the container was left under the same light source (white LED) as in Example 1, and light was emitted to 3-mercaptobutanoic acid through the container.

As shown in Table 3, the Hazen color number (APHA) of 3-mercaptobutanoic acid decreased over time after light emission started, and the APHA became 14 after 8 days.

Comparative Example 6

30 mL (34 g) of the same 3-mercaptobutanoic acid having an APHA 25 as in Example 9 was put into the same container as in Example 1 and sealed. Then, the container was wrapped with an aluminum foil and light-shielded and left under a light source (white LED) as in Example 1, and light was emitted to the container wrapped with an aluminum foil.

As shown in Table 3, the Hazen color number (APHA) of 3-mercaptobutanoic acid hardly changed even when light was emitted, and the APHA was 25 after 8 days.

Example 10

A compound represented by Formula (9) was synthesized by the method described in Patent Document 8. The Hazen color number (APHA) of the synthesized compound represented by Formula (9) was obtained. As a result, the APHA was 169. A light emission process of emitting light was performed the compound having an APHA of 169 and represented by Formula (9) by the following method.

That is, a light source was inserted into a 50 mL three-necked flask containing 50 mL (60 g) of the compound having an APHA of 169 and represented by Formula (9) and a stirring bar, and light was emitted to the compound represented by Formula (9) with stirring. As the light source, an LED light source device PER-AMP for a photochemical reaction (a wavelength of 470 nm and an output of 610 mW (commercially available from The Institute of Creative Chemistry Co., Ltd.)) was used in combination with an LED lamp PER-LED-470 and a power supply unit PER-AMP-N4.

As shown in Table 4, the Hazen color number (APHA) of the compound represented by Formula (9) decreased over time after light emission started, and the APHA became 43 after 7 hours.

TABLE 4

| | Time [days] | 0 | 1 | 3 | 7 | 24 |
|---|---|---|---|---|---|---|
| Example 10 | APHA | 169 | 75 | 56 | 43 | |
| Example 11 | | 169 | 86 | 62 | 42 | |
| Example 12 | | 169 | | | 168 | 149 |

Example 11

A light emission process was performed in the same manner as in Example 10 except that, as the light source, an LED light source device PER-AMP for a photochemical reaction (a wavelength of 385 nm and an output of 605 mW (commercially available from The Institute of Creative Chemistry Co., Ltd.)) was used in combination with an LED lamp PER-LED-385 and a power supply unit PER-AMP-N4.

As shown in Table 4, the Hazen color number (APHA) of the compound represented by Formula (9) decreased over time after light emission started, and the APHA became 42 after 7 hours.

Example 12

A light emission process was performed in the same manner as in Example 10 except that, as the light source, an LED light source device PER-AMP for a photochemical reaction (a wavelength of 325 nm and an output of 36 mW (commercially available from The Institute of Creative Chemistry Co., Ltd.)) was used in combination with an LED lamp PER-LED-325 and a power supply unit PER-AMP-D2.

As shown in Table 4, the Hazen color number (APHA) of the compound represented by Formula (9) decreased over time after light emission started, the APHA became 168 after 7 hours, and the APHA became 149 after 24 hours.

Table 5 summarizes thiol compounds in measurement targets (thiol compounds or compositions containing the same) in Example 1 to Example 12, and Comparative Example 1 to Comparative Example 6, the amounts of the measurement targets, the light sources, the time when the light emission process was performed (light emission time), and the Hazen color number (APHA) before the light emission process start and after the light emission process was completed.

TABLE 5

| | Measurement target | | | Light emission | APHA | |
|---|---|---|---|---|---|---|
| | Thiol compound | Amount | Light source | time | Before start | After completion |
| Example 1 | pentaerythritol tetrakis(3-mercaptobutyrate) | 50 mL | white LED | 30 days | 160 | 72 |
| Example 2 | pentaerythritol tetrakis(3-mercaptobutyrate) | 50 mL | sunlight | 30 days | 160 | 23 |
| Example 3 | pentaerythritol tetrakis(3-mercaptobutyrate)/toluene | 50 mL | white LED | 12 days | 67 | 37 |
| Example 4 | pentaerythritol tetrakis(3-mercaptobutyrate)/acetonitrile | 50 mL | white LED | 12 days | 100 | 37 |
| Example 5 | Karenz MT BD1 | 30 mL | white LED | 8 days | 57 | 38 |
| Example 6 | Karenz MT NR1 | 30 mL | white LED | 8 days | 45 | 36 |
| Example 7 | Karenz MT TPMB | 30 mL | white LED | 8 days | 42 | 31 |
| Example 8 | Karenz MT PE1 | 30 mL | white LED | 8 days | 57 | 32 |
| Example 9 | 3-mercaptobutanoic acid | 30 mL | white LED | 8 days | 25 | 14 |
| Example 10 | pentaerythritol tetrakis(3-mercaptobutyrate) | 50 mL | 470 nm LED | 7 hours | 169 | 43 |
| Example 11 | pentaerythritol tetrakis(3-mercaptobutyrate) | 50 mL | 385 nm LED | 7 hours | 169 | 42 |
| Example 12 | pentaerythritol tetrakis(3-mercaptobutyrate) | 50 mL | 325 nm LED | 24 hours | 169 | 149 |
| Comparative Example 1 | pentaerythritol tetrakis(3-mercaptobutyrate) | 50 mL | white LED (light shield) | 30 days | 160 | 158 |
| Comparative Example 2 | Karenz MT BD1 | 30 mL | white LED (light shield) | 8 days | 57 | 58 |
| Comparative Example 3 | Karenz MT NR1 | 30 mL | white LED (light shield) | 8 days | 45 | 46 |
| Comparative Example 4 | Karenz MT TPMB | 30 mL | white LED (light shield) | 8 days | 42 | 42 |

TABLE 5-continued

| | Measurement target | | | Light emission time | APHA | |
|---|---|---|---|---|---|---|
| | Thiol compound | Amount | Light source | | Before start | After completion |
| Comparative Example 5 | Karenz MT PE1 | 30 mL | white LED (light shield) | 8 days | 57 | 56 |
| Comparative Example 6 | 3-mercaptobutanoic acid | 30 mL | white LED (light shield) | 8 days | 25 | 25 |

As shown in Table 5, in Example 1 to Example 12, it was confirmed that, when the light emission process was performed, the Hazen color number (APHA) of the thiol compound or the composition containing the same decreased, and coloring was reduced.

On the other hand, in Comparative Example 1 to Comparative Example 6 in which light was shielded and the light emission process was performed, a decrease in the Hazen color number (APHA) of the thiol compound or the composition containing the same when the light emission process was performed was not confirmed.

The invention claimed is:

1. A method for producing a thiol compound, comprising a light emission process in which light is emitted to a colored thiol compound or a composition containing the colored thiol compound, wherein the colored thiol compound has a Hazen color number of 10 or more, and the thiol compound includes one or both of 3-mercaptocarboxylic acid and 3-mercaptocarboxylic acid ester.

2. The method for producing a thiol compound according to claim 1, wherein the light includes light with a wavelength of 250 nm to 600 nm.

3. The method for producing a thiol compound according to claim 1, wherein the Hazen color number of the thiol compound or the composition is 100 or more, and wherein the light emission process is performed until the Hazen color number of the thiol compound or the composition is less than 100.

4. The method for producing a thiol compound according to claim 1, wherein the thiol compound includes a thiol having at least one secondary mercapto group.

5. The method for producing a thiol compound according to claim 1, wherein the thiol compound includes one or both of 3-mercaptobutanoic acid and 3-mercaptobutanoic acid ester.

6. The method for producing a thiol compound according to claim 5, wherein the 3-mercaptobutanoic acid ester is any one of compounds represented by the following Formulae (3) and (4):

[Chem. 1]

(3)

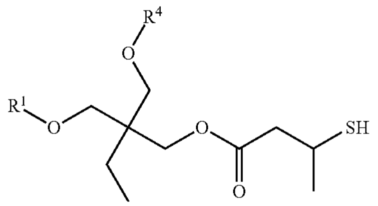

(4)

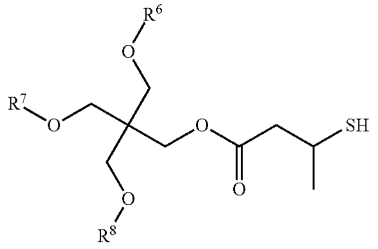

(5)

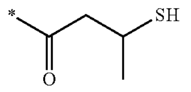

(in Formula (3), $R^4$ and $R^5$ each independently represent a hydrogen atom or a group represented by Formula (5))

(in Formula (4), $R^6$, $R^7$, and $R^8$ each independently represent a hydrogen atom or a group represented by Formula (5))

(in Formula (5), * indicates bonding positions for compounds represented by Formulae (3) and (4)).

7. The method for producing a thiol compound according to claim 5, wherein the 3-mercaptobutanoic acid ester is a compound represented by the following Formula (9):

[Chem. 2]

(9)

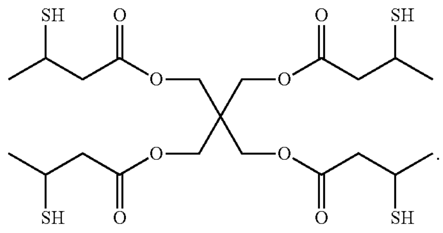

8. The method for producing a thiol compound according to claim 1, wherein the composition contains the thiol compound and at least one solvent selected from the group consisting of toluene, xylene, cyclohexane, methylcyclohexane, acetonitrile, methanol, ethanol, n-propanol, isopropanol, n-butanol, isobutanol, methyl acetate, ethyl acetate, butyl acetate, acetone, methyl ethyl ketone, methyl isobutyl ketone, cyclohexanone, ethylene glycol dimethyl ether, ethylene glycol monoethyl ether, ethylene glycol monobutyl ether, ethylene glycol monobutyl ether acetate, propylene glycol monomethyl ether, propylene glycol monomethyl ether acetate, and water.

9. The method for producing a thiol compound according to claim 2, wherein the Hazen color number of the thiol compound or the composition is 100 or more, and wherein the light emission process is performed until the Hazen color number of the thiol compound or the composition is less than 100.

10. The method for producing a thiol compound according to claim 2, wherein the thiol compound includes a thiol having at least one secondary mercapto group.

11. The method for producing a thiol compound according to claim 3, wherein the thiol compound includes a thiol having at least one secondary mercapto group.

12. The method for producing a thiol compound according to claim 9, wherein the thiol compound includes a thiol having at least one secondary mercapto group.

13. The method for producing a thiol compound according to claim 2, wherein the composition contains the thiol compound and at least one solvent selected from the group consisting of toluene, xylene, cyclohexane, methylcyclohexane, acetonitrile, methanol, ethanol, n-propanol, isopropanol, n-butanol, isobutanol, methyl acetate, ethyl acetate, butyl acetate, acetone, methyl ethyl ketone, methyl isobutyl ketone, cyclohexanone, ethylene glycol dimethyl ether, ethylene glycol monoethyl ether, ethylene glycol monobutyl ether, ethylene glycol monobutyl ether acetate, propylene glycol monomethyl ether, propylene glycol monomethyl ether acetate, and water.

14. The method for producing a thiol compound according to claim 3, wherein the composition contains the thiol compound and at least one solvent selected from the group consisting of toluene, xylene, cyclohexane, methylcyclohexane, acetonitrile, methanol, ethanol, n-propanol, isopropanol, n-butanol, isobutanol, methyl acetate, ethyl acetate, butyl acetate, acetone, methyl ethyl ketone, methyl isobutyl ketone, cyclohexanone, ethylene glycol dimethyl ether, ethylene glycol monoethyl ether, ethylene glycol monobutyl ether, ethylene glycol monobutyl ether acetate, propylene glycol monomethyl ether, propylene glycol monomethyl ether acetate, and water.

15. The method for producing a thiol compound according to claim 4, wherein the composition contains the thiol compound and at least one solvent selected from the group consisting of toluene, xylene, cyclohexane, methylcyclohexane, acetonitrile, methanol, ethanol, n-propanol, isopropanol, n-butanol, isobutanol, methyl acetate, ethyl acetate, butyl acetate, acetone, methyl ethyl ketone, methyl isobutyl ketone, cyclohexanone, ethylene glycol dimethyl ether, ethylene glycol monoethyl ether, ethylene glycol monobutyl ether, ethylene glycol monobutyl ether acetate, propylene glycol monomethyl ether, propylene glycol monomethyl ether acetate, and water.

16. The method for producing a thiol compound according to claim 7, wherein the composition contains the thiol compound and at least one solvent selected from the group consisting of toluene, xylene, cyclohexane, methylcyclohexane, acetonitrile, methanol, ethanol, n-propanol, isopropanol, n-butanol, isobutanol, methyl acetate, ethyl acetate, butyl acetate, acetone, methyl ethyl ketone, methyl isobutyl ketone, cyclohexanone, ethylene glycol dimethyl ether, ethylene glycol monoethyl ether, ethylene glycol monobutyl ether, ethylene glycol monobutyl ether acetate, propylene glycol monomethyl ether, propylene glycol monomethyl ether acetate, and water.

* * * * *